US008828006B2

(12) United States Patent
Semler et al.

(10) Patent No.: US 8,828,006 B2
(45) Date of Patent: Sep. 9, 2014

(54) ANTI-SPLAY APPARATUS

(75) Inventors: Mark E. Semler, Morris Plains, NJ (US); Bruce Frankel, Mount Pleasant, SC (US)

(73) Assignee: BlackStone Medical, Inc., Lewisville, TX (US)

( * ) Notice: Subject to any disclaimer, the term of this patent is extended or adjusted under 35 U.S.C. 154(b) by 206 days.

(21) Appl. No.: 12/707,382

(22) Filed: Feb. 17, 2010

(65) Prior Publication Data

US 2011/0202095 A1    Aug. 18, 2011

(51) Int. Cl.
*A61B 17/70* (2006.01)
*A61B 17/86* (2006.01)
*A61B 19/00* (2006.01)

(52) U.S. Cl.
CPC ......... *A61B 17/708* (2013.01); *A61B 2019/307* (2013.01); *A61B 17/7085* (2013.01)
USPC .......................... 606/86 A; 606/308; 606/305

(58) Field of Classification Search
USPC ................ 606/305–308, 319, 328, 273, 86 A
See application file for complete search history.

(56) References Cited

U.S. PATENT DOCUMENTS

| | | | |
|---|---|---|---|
| 7,160,300 B2 | 1/2007 | Jackson | |
| 7,311,733 B2 | 12/2007 | Metz-Stavenhagen | |
| 7,465,306 B2 | 12/2008 | Pond, Jr. et al. | |
| 8,002,798 B2 * | 8/2011 | Chin et al. | 606/246 |
| 2005/0131408 A1 | 6/2005 | Sicvol et al. | |
| 2005/0192570 A1 | 9/2005 | Jackson | |
| 2005/0261687 A1 * | 11/2005 | Garamszegi et al. | 606/61 |
| 2006/0058794 A1 * | 3/2006 | Jackson | 606/61 |
| 2006/0111712 A1 | 5/2006 | Jackson | |
| 2006/0111713 A1 | 5/2006 | Jackson | |
| 2008/0051794 A1 * | 2/2008 | Dec et al. | 606/73 |
| 2008/0119849 A1 | 5/2008 | Beardsley et al. | |
| 2008/0119850 A1 | 5/2008 | Sicvol et al. | |
| 2008/0228228 A1 | 9/2008 | Hestad et al. | |
| 2008/0243190 A1 | 10/2008 | Dziedzic et al. | |
| 2008/0275456 A1 | 11/2008 | Vonwiller et al. | |
| 2008/0288005 A1 | 11/2008 | Jackson | |
| 2008/0300638 A1 | 12/2008 | Beardsley et al. | |
| 2009/0005814 A1 | 1/2009 | Miller et al. | |
| 2010/0114179 A1 * | 5/2010 | Moore et al. | 606/308 |
| 2010/0174325 A1 * | 7/2010 | Won et al. | 606/305 |
| 2011/0087293 A1 * | 4/2011 | Ferreira et al. | 606/265 |

FOREIGN PATENT DOCUMENTS

WO    2007149426    12/2007

OTHER PUBLICATIONS

Search Report from corresponding European Patent Application No. 11154063.9 dated Jun. 8, 2011.
Australian Examination Report No. 1, AU Application No. 2011200513, dated Jan. 3, 2014, 3 pages.

* cited by examiner

*Primary Examiner* — Eduardo C Robert
*Assistant Examiner* — Julianna N Harvey
(74) *Attorney, Agent, or Firm* — Baker & McKenzie LLP

(57) ABSTRACT

An anti-splay apparatus having a bridge and frangible connection points for use with mechanical fasteners having a shank portion and a receiving member with opposing arms is provided. The bridge may take a number of forms including a ring, a notched ring, a tube, or a notched tube and the connection points join the opposing arms of the receiving member with the bridge. Also provided is the anti-splay apparatus also having tabs connected between frangible connection points.

6 Claims, 5 Drawing Sheets

ANTI-SPLAY APPARATUS

TECHNICAL FIELD

Embodiments of the apparatus and system disclosed herein relate generally to an anti-splay apparatus having frangible tab sections for use with mechanical fastener receiving members having opposed arms. More specifically, disclosed herein is an anti-splay apparatus that comprises a bridge removably attached to opposing arms of a receiving member by way of two or more frangible tabs.

BACKGROUND

A number of mechanical screws and fasteners are used to fuse, fixate or fasten to bone. Such fasteners are used particularly frequently in correcting spinal problems. One well known set of mechanical fasteners includes pedicle screw assemblies which are used to align and/or fix a desired spatial relationship between vertebral bodies. Pedicle screws have a shape and size that is configured to attach to pedicle bone. Pedicle screw assemblies typically include a threaded shank that is adapted to be threaded into a vertebra, and a receiving member usually in the form of a U-shaped head.

Referring to FIG. 1, a known reduction screw style pedicle screw assembly 1 is illustrated. Pedicle screws used for spinal surgery generally include a shank 3 and a receiving member 5. Receiving member 5 typically includes a U-Shaped head 7 from which two opposing arms 9 extend. In some prior art pedicle screw assemblies, extended portions 11 are permanently (with a frangible connection) or removably attached to and extend upwardly from the opposing arms 9. Shown in FIG. 1 are distal frangible connection points 10 attaching the extended portions 11 to opposing arms 9. Such distal frangible connection points 10 may be used to break off extended portions 11 from the reduction screw leaving the opposing arms 9, U-shaped head 7 and shank 3. An ordinarily skilled artisan that distal frangible connection points may be utilized on any style of reduction screw assemblies or mechanical fastening systems having the general shape of a shank and receiving member.

A set-screw, plug, or similar type of fastening mechanism is used to lock the spinal connector, e.g., a spinal rod, into the receiving head of the pedicle screw. In use, the shank of each screw is threaded into a vertebra, and once properly positioned, a rod is seated through the receiving member of each screw and the rod is locked in place by tightening a cap or other fastener mechanism to securely interconnect each screw and the spinal rod.

In general, pedicle screw assemblies use two or more pedicle screws which are secured to vertebra. After the screws are secured to the vertebra, the screws are coupled to a spinal stabilization rod that restricts movement of the stabilized vertebra. It is important that the screws have a secure coupling with the spinal stabilization rod in order to prevent movement of the rod relative to the screw after placement. The pedicle screws are coupled to the rods by way of the opposing arms of the receiving member.

One issue with the opposing arms of the receiving member is that they can splay, or spread apart while applying torque loads to the setscrew against the rod during what is commonly known as reduction and final tightening or torquing of the rod. Splaying can result in failure of the rod to remain in place relative to the shank portion.

A number of methods and structures have been employed to prevent splaying of the opposing arms of receiving members. Such structures include the use of a non-breakaway ring permanently affixed to the upper ends of the opposing arms (or extensions). When such structures are used, a surgeon must use a separate cutter to remove the ring upon completion of surgery so that the arms (or extensions) may be freed for removal. The cut portions are small, may be sharp and can become projectiles from the force of the cutting action.

In yet other known methods for preventing splaying, a ring is removably screwed or attached onto opposing arms (or extensions). Such methods require complex tools for manipulation of the ring and arms (or extensions).

What is needed is an anti-splay bridge which is removably coupled to the opposing arms (or extensions), and which may be readily removed without complex tools or manipulation and in a controlled manner.

SUMMARY

One embodiment provides an anti-splay apparatus comprising a bridge joining a plurality of opposing arms of a receiving member of a mechanical fastening assembly wherein the bridge is joined to the arms by a plurality of frangible connection points. In certain aspects, the anti-splay apparatus further comprises one of more tabs joined to the bridge at a location between frangible connection points. In some more specific aspects, the one or more tabs further comprise an opening or indentation. The tabs may have varying shapes in different embodiments of the apparatus and such shapes may include, but are not limited to, rectangular, square, hexagonal, or oval shapes.

In yet other embodiments, the bridge of the anti-splay apparatus comprises a ring, a tube, two or more arcs, a notched arc, a notched ring, a notched tube, or a combination thereof.

In some aspects of the anti-splay apparatus, the receiving member comprises two opposing arms. While in other aspects, the receiving member may include three or more opposing arms. In certain aspects of the apparatus, the receiving member further includes extensions which extend upwardly from the arms and effectively lengthen the arms.

In a particular embodiment, the anti-splay apparatus comprises a plurality of tabs wherein the bridge is ring-shaped and the tabs extend upwardly from the bridge and are connected to the bridge by four frangible connection points. In yet other particular embodiments, an upper portion of one or more of the plurality of opposing arms may include a depression.

In another particular embodiment, the anti-splay apparatus includes a plurality of bridge/tab combinations wherein each bridge/tab combination is attached between two arms of a receiving member of a mechanical fastening assembly by a pair of frangible connection points wherein the connection points of each pair are spaced apart laterally. In certain aspects, the bridge/tab combinations may be rectangular, square, oval, or hexagonal. In some embodiments, one or more of the plurality of bridge/tab combinations further comprises an opening or indentation.

In another particular embodiment, the anti-splay apparatus comprises a ring shaped bridge comprising a plurality of downwardly extending tabs wherein the bridge is attached to a plurality of opposing arms on a receiving member by a plurality of frangible connection points.

Yet other embodiments provide an improvement to a pedicle screw assembly comprising a shank and a receiving member comprising a U-shaped head having an opening through which the shank passes and wherein a plurality of arms extend upwardly from the U-shaped head, the improvement comprising a bridge joining the plurality wherein the bridge is joined to the arms by a plurality of frangible connection points. The improvement may further include one or more tabs joined to the bridge at a location between frangible connection points. The bridge of the improvement may comprise a ring, a tube, two or more arcs, a notched arc, a notched ring, a notched tube or a combination thereof. The one or more tabs of the improvement may further comprise an opening or indentation and may be rectangular, square, hexagonal, or oval.

In a particular embodiment, the improvement includes two tabs joined to the bridge by four frangible connection points. In certain embodiments of the improvement, the tabs are rectangular, the bridge is ring-shaped and the tabs extend upwardly from the bridge. While in other embodiments, the tabs are rectangular, the bridge is ring-shaped and the tabs extend downwardly from the bridge.

Particular embodiments of the apparatus and/or improvement may include scored sections on one or more frangible connection points. In some embodiments, such scored sections control the location of the break within the frangible connection point and/or control the size and shape of any connection point or bridge material remaining on the arms or extensions following a break.

BRIEF DESCRIPTION OF THE DRAWINGS

The invention may be more fully understood from the following detailed description taken in conjunction with the accompanying drawings, in which.

DETAILED DESCRIPTION

Certain exemplary embodiments are described below to provide an overall understanding of the principles of the structure, function, and use of the apparatus disclosed herein. One or more examples of these embodiments are illustrated in the accompanying drawings. Those of ordinary skill in the art will understand that the apparatus specifically described and illustrated herein are non-limiting exemplary embodiments and that the scope of the present invention is defined solely by the claims. The feature illustrated or described in connection with one exemplary embodiment may be combined with the features of other embodiments. Such modifications and variations are intended to be included within the scope of the inventive apparatus.

Embodiments of the invention provide an apparatus to prevent splaying of two opposing arms of a receiving member used in mechanical fastening assemblies. Such mechanical fastening assemblies are generally useful in minimally invasive surgical techniques. For exemplary purposes and not by way of limitation, the mechanical fastening assembly is discussed as a pedicle screw.

Figure 1:
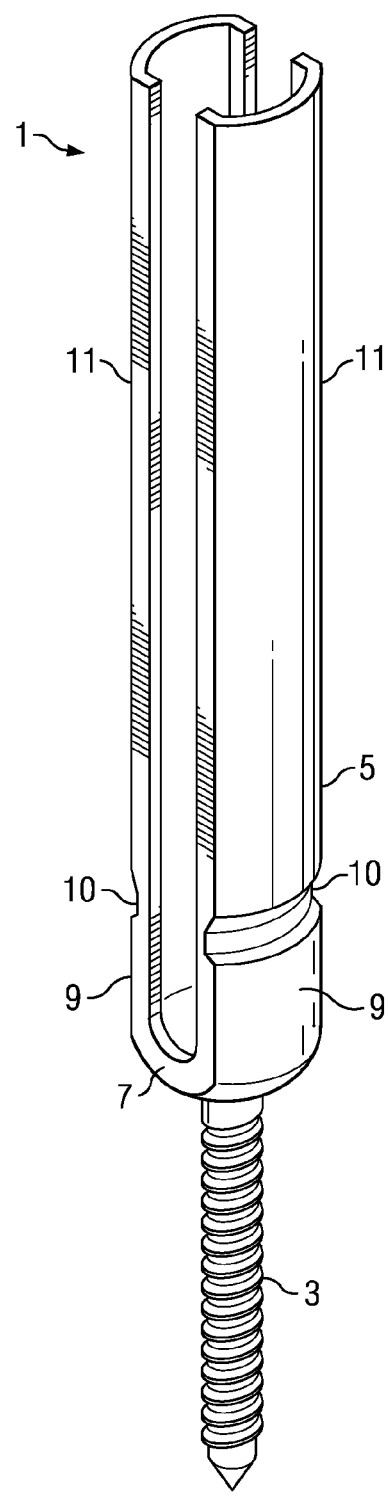
FIG. 1 is an elevational view of a pedicle screw assembly of a type known in the art.
Figure 2:
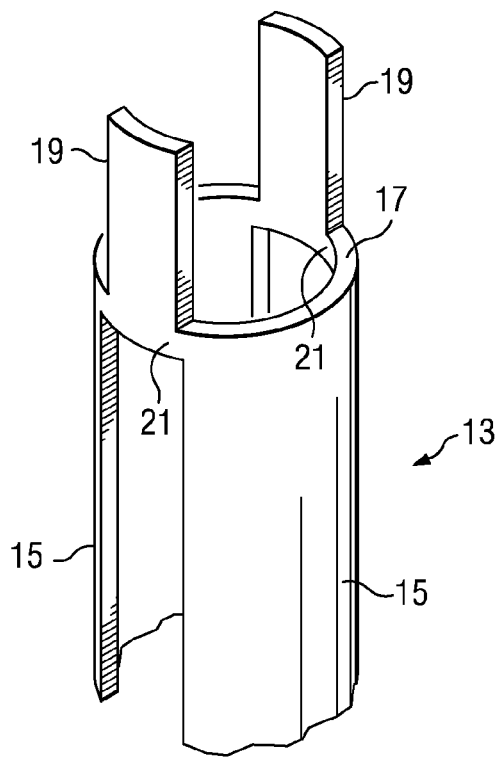
FIG. 2 is a perspective view of a first embodiment of the anti-splay apparatus having a ring-shaped bridge removably coupled to opposing arms of a receiving member.

Referring to FIG. 2 a first embodiment of the anti-splay apparatus 13 is illustrated. Two opposing arms (or extensions) 15 extend upwardly from a head (not shown) through which a shank (not shown) may be connected. The anti-splay apparatus 13 includes a bridge 17 in the shape of a ring joining arms 15 at a top surface of the arms. Two tabs 19 extend upwardly from the bridge 17 and are spaced from the arms 15 by frangible connection points 21. As shown in FIG. 2, tabs 19 are rectangular shaped and may, in some embodiments, be curved along a longitudinal axis to mimic the shape of arms (or extensions) 15. Tabs 19 may take any of a number of shapes, including for example, square, oval, or semicircular. Frangible connection points 21 are integrally formed with bridge 17 but have sufficiently narrow width and height such that they may be readily broken or snapped. In some embodiments, frangible connection points 21 have a width and/or height of no greater than 1 mm. In yet other embodiments, the frangible connection points 21 may further include grooves or carved areas to further control or promote breakage. As can be seen from FIG. 2, in some embodiments, a portion of the bridge may be an upper portion or surface of the arms (or extensions) 15.

Figure 3:
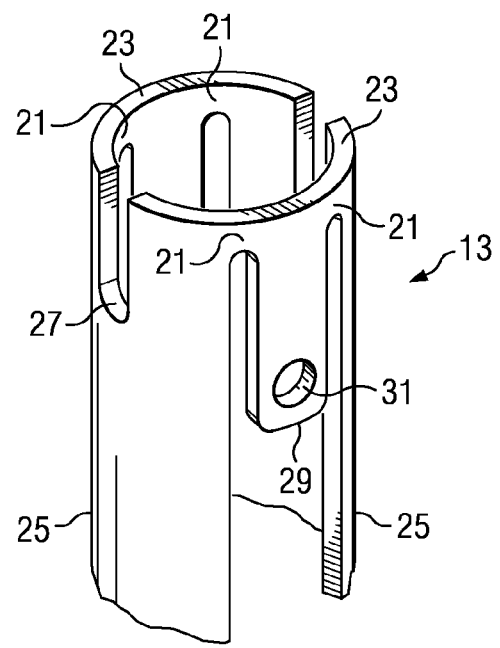
FIG. 3 is a perspective view of a second embodiment of the anti-splay apparatus having two semi-circular bridge portions removably coupled across opposing arms of a receiving member.

A second embodiment of the anti-splay apparatus 13 is shown in FIG. 3. In the second illustrated embodiment, the bridge is formed from two semicircular portions 23 spanning and connecting two opposing arms (or extensions) 25. As shown in FIG. 3, an uppermost portion of the arms (or extensions) 25 may have depressions 27. Downwardly projecting tabs 29 extend between frangible connection points 21. Tabs 29 are rectangular and may be curved away from a longitudinal axis to mimic the shape of arms (or extensions) 25. Tabs 29 may include an opening or indentation 31 to permit the tabs to be hooked or grabbed with a tool. Depressions 27 may, in some embodiments, allow torque applied to the arms (or extensions) 25 upon flexing and removal of said tabs 25.

Figure 8:
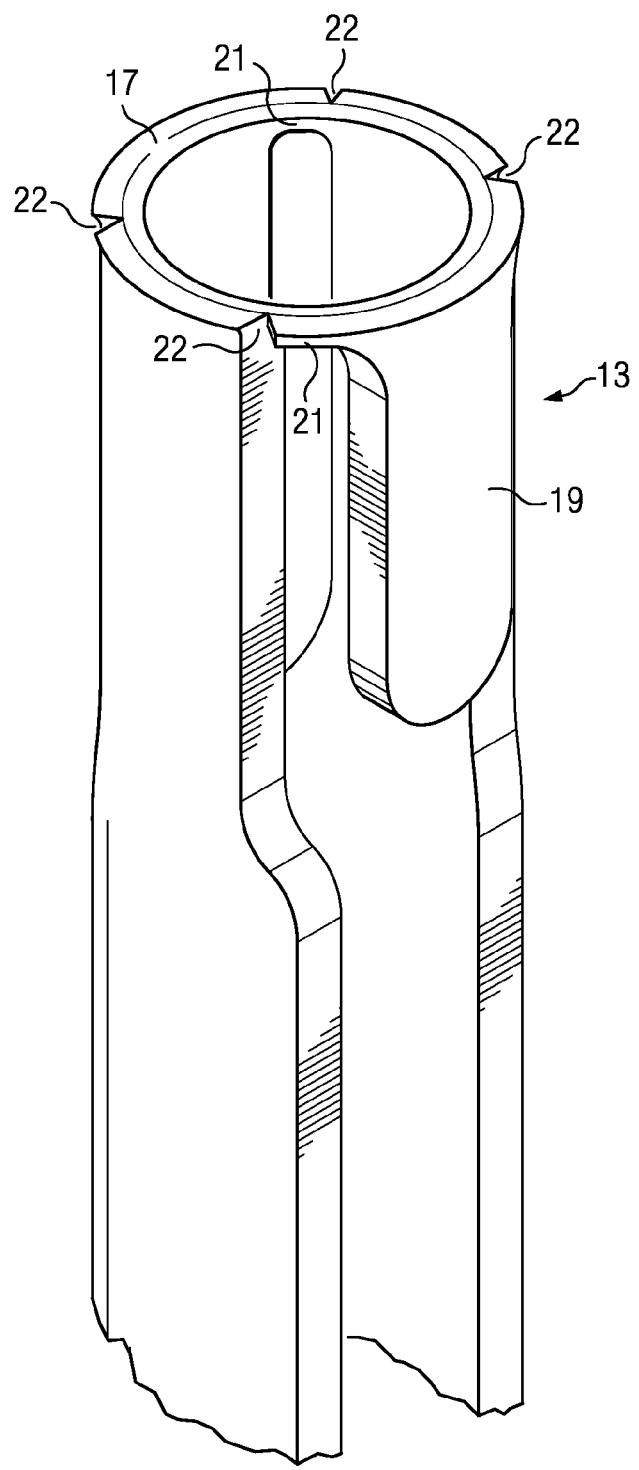
FIG. 8 is a perspective view of the embodiment of FIG. 3 further illustrating the use of scored sections.

FIG. 8 illustrates the embodiment of FIG. 3 further including a scored section 22 on each of connection points 21. It would be understood by an ordinarily skilled artisan that such scored sections may appear on one or more connection points of an anti-splay apparatus, including embodiments of the apparatus other than that shown in FIG. 3. Without being bound by any particular theory, scored sections 22 may be used to better control the location of the break of the frangible connection points 21 upon flexing of tabs or bridge/tab combinations. In some instances, scored sections 22 may also be used to control the amount and shape of material remaining following a break in a connection point. In yet other embodiments, however, no scored sections 22 may be used and the break location and remaining material following a break may be controlled solely by the dimensions of the frangible connection points and/or direction or angle of twist applied to the frangible connection points.

Figure 4:
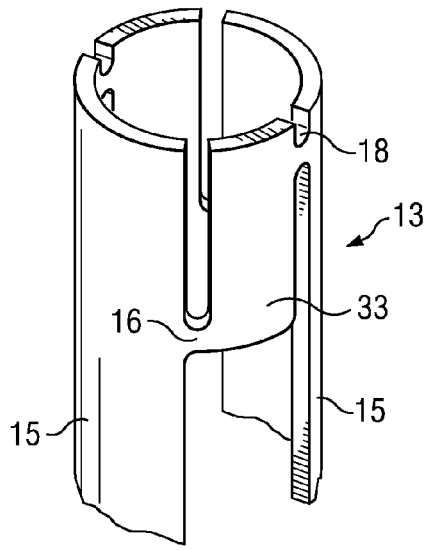
FIG. 4 is a perspective view of a third embodiment of the anti-splay apparatus having a broken tubular bridge removably coupled to opposing arms of a receiving member by way of non-symmetrical frangible tabs.

Referring to FIG. 4, a third embodiment of the anti-splay apparatus 13 includes bridge/tab combinations 33. Bridge/tab combinations 33 are rectangular in shape and attach to two opposing arms (or extensions) 15 by way of a pair of frangible connection points which are spaced apart laterally. In some embodiments, the frangible connection points are further spaced unequally from a top surface of the arms (or extensions) 15. That is, one of a pair of frangible connection points joining a bridge/tab combination to the arms (or extensions) 15 may constitute a deep recess or depression 16 while the second one of such pair may constitute a shallow recess or depression 18. In some embodiments, bridge/tab combinations 33 may have different shapes; for example, square, oval, or hexagonal. In certain embodiments, bridge/tab combinations 33 may further include an opening or indentation (not shown) to facilitate hooking and flexing the bridge/tab combinations to cause frangible connection points 21 to break.

Figure 5:
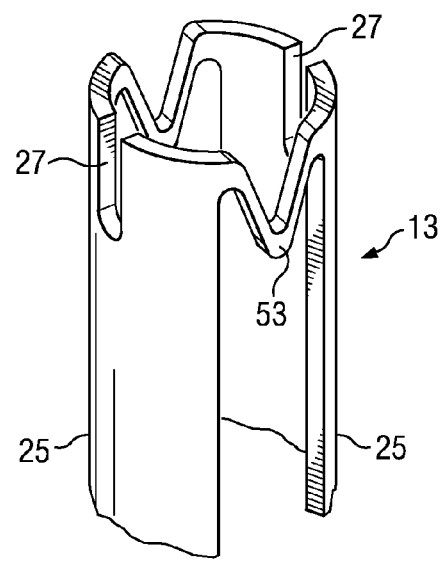
FIG. 5 is a perspective view of a fourth embodiment of the anti-splay apparatus having a notched bridge removably coupled across opposing arms of a receiving member.

A fourth embodiment of the anti-splay apparatus 13 is illustrated in FIG. 5. Arms (or extensions) 25 are joined by an alternative bridge/tab combination 53 which is a substantially V-shaped or U-shaped member. Bridge/tab combination 53 may have dimensions similar to or greater than frangible connection points 21.

Figure 6:
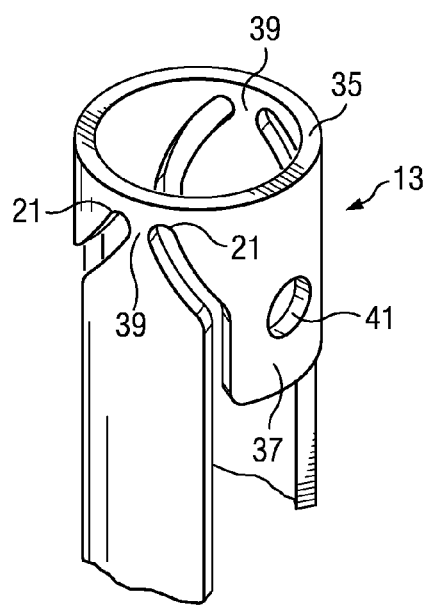
FIG. 6 is a perspective view of a fifth embodiment of the anti-splay apparatus having a notched tubular bridge removably coupled to opposing arms of a receiving member.

Referring to FIG. 6, a fifth embodiment of the anti-splay apparatus 13 is shown. A ring shaped bridge 35 is attached to a top surface of arms (or extensions) 39. Extending downward from the bridge 35 are opposing tabs 37. Tabs 37 partially span the separation between arms (or extensions) 39 and join the bridge 35 at the two frangible connection points 21. As shown in FIG. 6, bridge 35 and tabs 37 extend axially beyond arms (or extensions) 39. In other embodiments, bridge 35 and tabs 37 may be co-axial with arms (or extensions) 39. One or both tabs 37 may further include an opening or indentation 41 such that it may be readily hooked or grabbed with a tool to cause flexing and breaking of frangible connection points 21. FIG. 6 displays a top section of arms (or extensions) 39 that slopes inwardly. In alternative embodiments, an upper portion of arms (or extensions) 39 may taper in a stepwise fashion.

In each of FIGS. 3 and 5, a depression 27 is shown in each of arms 25. In such embodiments, depressions 27 may assist in applying torque applied to the arms 25 when the tab 29 or bridge/tab combination 53 is flexed so as to break the connection attaching arms 25 proximately above the U-shaped receiving member of the distal screw body.

Figure 7:
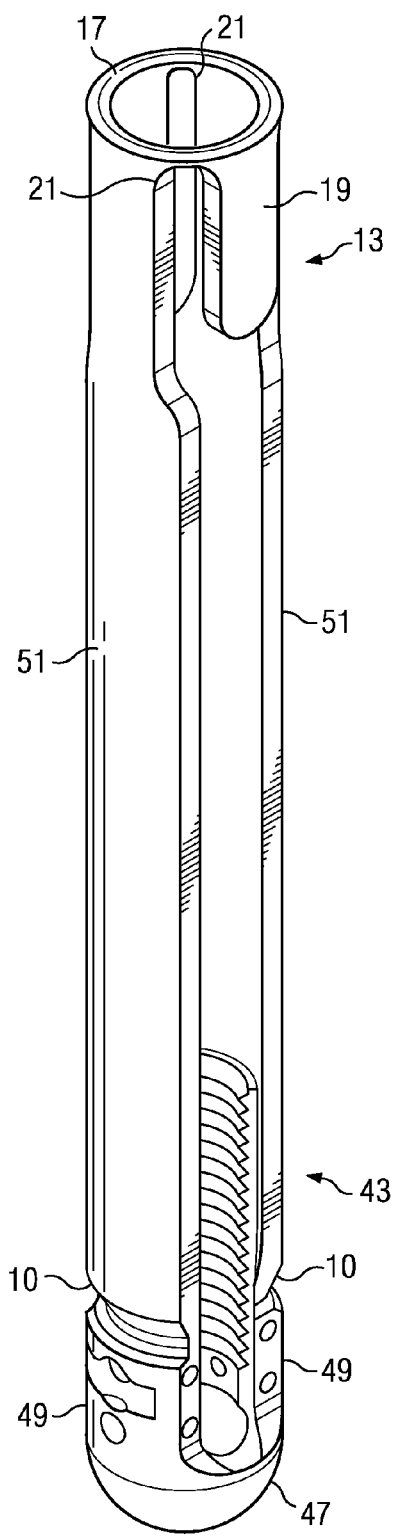
FIG. 7 is a perspective view of the second embodiment of the anti-splay apparatus shown in FIG. 3 and including extensions and distal connection points.

FIG. 7 illustrates the second embodiment (without optional scored section 22) of the inventive anti-splay apparatus 13 used in connection with and integrally formed with a receiving member 43 of a pedicle screw assembly. The pedicle screw assembly includes a receiving member 43 including a U-shaped head 47 and opposing arms 49 with extensions 51. The assembly illustrated in FIG. 7 further shows distal connection points 10. In use, bridge 17 prevents arms 49 and extensions 51 from splaying when the pedicle screw assembly is put into place. Once the placement of the pedicle screw assembly is completed, tabs 19 may be gripped with a simple tool or by hand, and flexed so as to break frangible connection points 21. As shown in FIG. 7, U-shaped head 47 may have one or more openings or features known in the art.

One of ordinary skill in the art would understand that the various embodiments of the anti-splay apparatus, including but not limited to those shown in FIGS. 2-6 may be used with any of a number of mechanical fastening assemblies provided such assemblies include a receiving member having two or more arms (or extensions). That is the anti-splay apparatus may be attached to or integrally molded with any such known or later developed receiving member.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An anti-splay apparatus, comprising:
a head that secures to a bone by a shank, the shank extending from the head in a first direction when the head is secured to the bone by the shank;
a plurality of opposing arms of a receiving member of a mechanical fastening assembly, the plurality of opposing arms extending from the head in a second direction different from the first direction;
a bridge proximal to an end of the plurality of opposing arms distal to the head, the bridge joining the plurality of opposing arms wherein the bridge is joined to the arms by a plurality of frangible connection points; and
one of more tabs joined to the bridge at a location between frangible connection points,
wherein the one or more tabs are rectangular, square, hexagonal, or oval.

2. An anti-splay apparatus, comprising:
a head that secures to a bone by a shank, the shank extending from the head in a first direction when the head is secured to the bone by the shank;
two arms of a receiving member of a mechanical fastening assembly, the two arms extending from the head in a second direction different from the first direction; and
a plurality of bridge/tab combinations proximal to an end of the arms distal to the head wherein each bridge/tab combination is attached between the two arms by a pair of frangible connection points wherein the frangible connection points of each pair are spaced apart laterally,
wherein the bridge/tab combinations are rectangular, square, oval, or hexagonal.

3. An anti-splay apparatus, comprising:
a head that secures to a bone by a shank, the shank extending from the head in a first direction when the head is secured to the bone by the shank;
a plurality of opposing arms on a receiving member, the plurality of opposing arms extending from the head in a second direction different from the first direction; and
a ring shaped bridge proximal to an end of the plurality of opposing arms distal to the head, the bridge comprising a plurality of downwardly extending tabs, and the bridge being attached to the plurality of opposing arms by a plurality of frangible connection points.

4. The anti-splay apparatus of claim 3 further comprising a scored section on one or more of the frangible connection points.

5. A pedicle screw assembly, comprising:
a shank;
a receiving member comprising a U-shaped head having an opening through which the shank passes, the U-shape head being securable to a bone by the shank, and the shank extending from the U-shape head in a first direction when the U-shaped head is secured to the bone with the shank;
a plurality of arms that extend upwardly from the U-shaped head in a second direction different from the first direction;
a bridge proximal to an end of the plurality of arms distal to the U-shaped head, the bridge joining the plurality of arms wherein the bridge is joined to the arms by a plurality of frangible connection points; and
one or more tabs joined to the bridge at a location between frangible connection points,
wherein the one or more tabs are rectangular, square, hexagonal, or oval.

6. A pedicle screw assembly, comprising:
a shank;
a receiving member comprising a U-shaped head having an opening through which the shank passes, the U-shape head being securable to a bone by the shank, and the shank extending from the U-shape head in a first direction when the U-shaped head is secured to the bone with the shank;
a plurality of arms that extend upwardly from the U-shaped head in a second direction different from the first direction;
a bridge proximal to an end of the plurality of arms distal to the U-shaped head, the bridge joining the plurality of arms wherein the bridge is joined to the arms by a plurality of frangible connection points; and
one or more tabs joined to the bridge at a location between frangible connection points,
wherein there are two tabs joined to the bridge by four frangible connection points.

* * * * *